(12) United States Patent  
Vitusevich et al.

(10) Patent No.: US 10,859,529 B2  
(45) Date of Patent: Dec. 8, 2020

(54) DEVICE AND METHOD FOR MEASURING SMALL VOLTAGES AND POTENTIALS ON A BIOLOGICAL, CHEMICAL OR OTHER SAMPLE

(71) Applicant: FORSCHUNGSZENTRUM JUELICH GMBH, Juelich (DE)

(72) Inventors: Svetlana Vitusevich, Dueren (DE); Jing Li, Juelich (DE); Sergli Pud, Juelich (DE)

(73) Assignee: Forschungszentrum Juelich GmbH, Juelich (DE)

( * ) Notice: Subject to any disclaimer, the term of this patent is extended or adjusted under 35 U.S.C. 154(b) by 470 days.

(21) Appl. No.: 15/033,235

(22) PCT Filed: Oct. 15, 2014

(86) PCT No.: PCT/DE2014/000515  
§ 371 (c)(1),  
(2) Date: Apr. 29, 2016

(87) PCT Pub. No.: WO2015/067231  
PCT Pub. Date: May 14, 2015

(65) Prior Publication Data  
US 2016/0274055 A1    Sep. 22, 2016

(30) Foreign Application Priority Data

Nov. 9, 2013  (DE) .................. 10 2013 018 850

(51) Int. Cl.  
*G01N 27/414* (2006.01)  
*G01N 33/543* (2006.01)

(52) U.S. Cl.  
CPC ... *G01N 27/4145* (2013.01); *G01N 33/54373* (2013.01); *G01N 27/4146* (2013.01)

(58) Field of Classification Search  
CPC ........... G01N 27/4145; G01N 27/4146; G01N 33/54373  
See application file for complete search history.

(56) References Cited

U.S. PATENT DOCUMENTS

| 2003/0001881 A1 | 1/2003 | Mannheimer et al. |
| 2006/0231754 A1 | 10/2006 | Wang et al. |

(Continued)

FOREIGN PATENT DOCUMENTS

| DE | 10 2010 021 078 | 11/2011 |
| DE | 10 2011 102 854 | 2/2012 |

(Continued)

OTHER PUBLICATIONS

Zayats, Maya, et al. "Imprinting of specific molecular recognition sites in inorganic and organic thin layer membranes associated with ion-sensitive field-effect transistors." Tetrahedron 58.4 (2002): 815-824.*

(Continued)

*Primary Examiner* — Robert J Eom  
(74) *Attorney, Agent, or Firm* — Norris McLaughlin, P.A.

(57) ABSTRACT

A device and a method for measuring small voltages and potentials on biological, chemical and other samples. The device comprises at least one field effect transistor including a source, a drain, a gate that is in contact with the sample and insulated by a gate dielectric from the conducting channel of the field effect transistor, means for applying a voltage between the source and the drain, and means for applying a bias voltage to the gate. The gate dielectric includes at least one attachment site in the interior thereof, which is able to trap charge carriers from the channel and, conversely, to release these to the channel. Such an attachment site superimposes the current flowing through the channel, and thus through the transistor, with a telegraph modulation signal by continuously statistically exchanging charge carriers with (Continued)

the channel, the characteristic time constants of the telegraph modulation signal being usable as a measuring signal for the potential or voltage of the sample instead of the previously used average time value of the drain current. In this way, a larger portion of the measured information is evaluated with respect to the required result, which considerably improves the sensitivity and accuracy of the measurement.

10 Claims, 5 Drawing Sheets

(56) References Cited

U.S. PATENT DOCUMENTS

| | | | |
|---|---|---|---|
| 2007/0128810 A1 | 6/2007 | Kao | |
| 2010/0244157 A1 | 9/2010 | Hirano et al. | |
| 2012/0065920 A1 | 3/2012 | Nagumo et al. | |

FOREIGN PATENT DOCUMENTS

| | | |
|---|---|---|
| DE | 10 2010 062 224 | 5/2012 |
| JP | H08-278281 A | 10/1996 |
| JP | 2008-166607 A | 7/2008 |
| JP | 2010-226037 A | 10/2010 |
| JP | 2010-238242 A | 10/2010 |
| JP | 2011-085557 A | 4/2011 |
| JP | 2012-060016 A | 3/2012 |
| WO | 2006/103872 A1 | 10/2006 |
| WO | WO-2013/025429 | 2/2013 |

OTHER PUBLICATIONS

Lin, Chen-Fu, et al. "A CMOS-Compatible Biological Transducer for Creatinine Detection: MIP-Gate ISFET." 2009 IEEE Circuits and Systems International Conference on Testing and Diagnosis. IEEE, 2009.*

Pan, Tung-Ming, and Kao-Ming Liao. "Comparison of structural and sensing characteristics of Pr2O3 and PrTiO3 sensing membrane for pH-ISFET application." Sensors and Actuators B: Chemical 133.1 (2008): 97-104.*

Ito, Yoshitaka. "Long-term drift mechanism of Ta2O5 gate pH-ISFETs." Sensors and Actuators B: Chemical 64.1-3 (2000): 152-155.*

Liu, et al., "Determination of the Small Band Gap of Carbon Nanotubes Using the Ambipolar Random Telegraph Signal", Nano Letters, 2005, vol. 5, No. 7, pp. 1333-1336—(Cited in Chinese Office Action dated Nov. 1, 2017 in counterpart Chinese Patent Application No. 201480061357.9).

Wang, et al., "Effects of defects near source or drain contacts of carbon nanotube transistors", a Letters Journal Exploring the Crontiers of Physics, CPEL1650973P, EPL, 100 (2012), www.epljournal.org, pp. 1-5, Nov. 2012(Cited in Chinese Office Action dated Nov. 1, 2017 in counterpart Chinese Patent Application No. 201480061357.9).

Fei Liu et al: Determination of the Small Band Gap of Carbon Nanotubes Using the Ambipolar Random Telegraph Signal:, Nano Letters, vol. 5, No. 7, Jul. 1, 2005 (Jul. 1, 2005), pp. 1333-1336, XP055170634, ISSN: 1530-6984, DOI: 10.1021/n1050578e abstract; figures 1-5, pp. 1333, right-hand column, paragraph 1-paragraph 2 pp. 1334, left-hand column, paragraph 2.

& Fei Liu et al: "Giant random telegraph signals in the carbon nanotubes as a single defect probe", Applied Physics Letters, American Institute of Physics, US, vol. 86, No. 16, Apr. 11, 2005 (Apr. 11, 2005), pp. 163102-163102, XP012065133, ISSN: 0003-6951, DOI: 10.1063/1.1901822 abstract: figures 1-3, p. 1, right-hand column, paragraph 2-p. 3, left-hand column, paragraph 2.

Neng-Ping Wang et al: "Effects of defects near source or drain contacts of carbon nauotabe transistors", Europhysics Letters: A Letters Journal Exploring the Frontiers of Physics, Institute of Physics Publishing, Bristol, FR, vol. 100, No. 4, Dec. 3, 2012 (Dec. 3, 2012), p. 47009, XP020231212, ISSN: 0295-5075, DOI: 10.1209/0295-5075/100/47009 abstract; figures 1-4, p. 5, left-hand column, paragraph 2 p. 1, left-hand column, paragraph 2.

Clement N et al: "A silicon nanowire ion-sensitive field-effect transistor with elementary charge sensitivity", Applied Physics Letters, American Institute of Physics, US, vol. 98, No. 1, Jan. 6, 2011 (Jan. 6, 2011), pp. 14104-14104, XP012139118, ISSN: 0003-6951, DOI: 10.1063/1.3535958 abstract: figures 1-3, p. 1, left-hand column, paragraph 2-p. 2, right=hand column, paragraph 1, p. 3, right-hand column, paragraph 3.

F. Liu et al: "Study of Randon Telegraph Signals in Single-Walled Carbon Nanotube Field Effect Transistors", IEEE Transactions on Nanotechnology, vol. 5, No. 5, Sep. 1, 2006 )Sep. 1, 2006), pp. 441-445, XP055172397, ISSN: 1536-125X, DOI: 10.1109/TNANO.2006.880906 abstract: figure 1 p. 441, right-hand column, paragraph 2-p. 444, left-hand column, paragraph 1.

S. Sorgenfrei, C. Chiu, M. Johnston, C. Nuckolls, K. L. Shepard, "Debye Screening in Single-Molecule Carbon Nanotube Field-Effect Sensors", Nano Letters 2011 (11), 3739-3743 (2011).

* cited by examiner

DEVICE AND METHOD FOR MEASURING SMALL VOLTAGES AND POTENTIALS ON A BIOLOGICAL, CHEMICAL OR OTHER SAMPLE

The invention relates to a device and to a method for measuring small voltages and potentials on biological, chemical and other samples.

BACKGROUND OF THE INVENTION

Many properties of biological samples are related to the gain, loss or spatial reorganization of electrical charges and can thus be measured indirectly and non-invasively via changes in potentials that these charges cause when they approach a measuring device. Measuring devices of the type in question frequently include a field effect transistor, the gate of which is in contact with the sample. The sample changes the potential at the gate and thereby modulates the current that is driven through the transistor at a predefined drain/source voltage. The disadvantage is that the signal of such measurements is too low to examine small voltages and potentials on biological, chemical or other samples.

A measuring device is known from (S. Sorgenfrei, C. Chiu, M. Johnston, C. Nuckolls, K, L. Shepard, "Debye Screening in Single-Molecule Carbon Nanotube Field-Effect Sensors", Nano Letters 2011 (11), 3739-3743 (2011)) which uses a carbon nanotube as the field effect transistor. The nanotube is functionalized with a defect for the attachment of a biomolecule. The binding of a biomolecule to this defect site and the unbinding of the biomolecule from this defect site produce two-level telegraph noise in the current that is driven through the nanotube, which can be used to study the binding and unbinding kinetics.

It is the object of the invention to allow additional properties of samples, which are able to cause changes in potentials, to be quantitatively measured with greater accuracy than according to the existing prior art, beyond the kinetics of binding to and unbinding from a defect site.

SUMMARY OF THE INVENTION

Within the scope of the invention, a device for measuring small voltages and potentials or other electrical variables of a sample was developed. This device comprises at least one field effect transistor including a source, a drain, a gate that is in contact with the sample and insulated by a gate dielectric from the conducting channel of the field effect transistor, and means for applying a voltage between the source and the drain, and means for applying a bias voltage to the gate.

According to the invention, the gate dielectric includes at least one attachment site in the interior thereof, which is able to trap charge carriers from the channel and, conversely, release these to the channel.

Such an attachment site superimposes the current flowing through the channel, and thus through the transistor, with statistical, step-like fluctuations between two levels by continuously statistically exchanging charge carriers with the channel. These levels correspond to the two possible states of the attachment site, which is either occupied or not occupied by a charge carrier. Such fluctuations are normally undesirable in semiconductor electronics, so that efforts are undertaken to minimize these. Since the time curve of the fluctuations resembles that of a Morse signal on a telegraph line, the term "random telegraph noise" has become commonly accepted for this.

It was found that the probabilities for the exchange of charge carriers are dependent, with high sensitivity, on the relation of the potential at the location of the attachment site to the Fermi level. Even a minor change in potential caused by an approaching biomolecule drastically changes these probabilities. This manifests itself in characteristic variables of the fluctuations, in particular in the time constants for trapping and/or for the releasing of charge carriers by the attachment site. These time constants determine the respective duration for which each of the two current levels is present. A clear signal can already be measured before the biomolecule binds to the gate or even makes contact with it. The gate is generally not metallized. The sample is brought in direct contact with the gate dielectric, which optionally can be functionalized in several locations with additional molecules for binding sample molecules of interest.

The desired signal caused by the fluctuations, which is composed of sudden step-like transitions between discrete current levels, wherein each of the points of time of these transitions has a statistical distribution, is referred to hereafter as the telegraph modulation signal.

Contrary to the existing prior art, the telegraph modulation signal is not generated at the location where the sample interacts with the measuring device, but in the interior of the gate dielectric. The attachment site has no direct contact with the sample. Thus, when the characteristic of the telegraph modulation signal changes, this is caused by the change in potential effectuated by the sample alone, and is not influenced by other properties of the sample. Consecutive measurements conducted on different samples are therefore quantitatively comparable to each other.

The cause for the stronger signal compared to the prior art is that the two levels of the telegraph modulation signal are separated from each other by a larger energy gap. According to the state of the art, the two states differ only by the binding energy of the biomolecule to the defect site in the nanotube. A considerably larger amount of energy (Coulomb energy) is necessary to exchange a charge between the defect site in the gate dielectric used according to the invention and the channel. Additionally, the difference between these two levels also affects the current through the transistor to a greater degree by the attachment site being located close to the channel. The attachment of a biomolecule to the nanotube according to the state of the art is thus only mediated via image charge effects to the channel and, as a result, affects the current to a significantly lesser degree.

The action of the attachment site can be customized in a variety of ways to render the device particularly sensitive to certain measuring ranges of the potential. For example, shielding effects within the material of the gate dielectric may be used for this purpose. The amount of energy that is needed for exchanging a charge between the attachment site and the channel and the effective cross-section for this charge exchange can be predefined, among other things, by the position of the attachment site within the gate dielectric. At the same time, the Fermi level can be shifted within wide limits via the bias voltage at the gate. The gate dielectric can advantageously include multiple attachment sites, which differ in the amounts of energy for the charge exchange, so that it is possible to carry out measurements simultaneously in several measuring ranges. However, no more than five attachment sites should be active at the same time, so that signal contributions can still be reliably distinguished from each other.

In a particularly advantageous embodiment of the invention, the attachment site is a local defect in the gate dielectric. This may advantageously be introduced into the gate dielectric, in particular by way of a local depletion and/or defect of a connecting element of the gate dielectric, in particular by way of a local depletion and/or defect of oxygen, and/or by annealing and/or by combing various dielectric materials, such as silicon dioxide/$Ta_2O_5$, $SiO_2$/$Al_2O_3$ or $SiO_2$/high-k dielectric, or the like, by way of mechanical stress or other surface conditions between the channel and other materials, such as between Si and $Si_{1-x}Ge_x$;

by locally damaging the gate dielectric using ionizing radiation or electron radiation, and/or by implanting foreign ions into the gate dielectric, and/or by way of mechanical compressive and/or tensile stress, and/or by injecting hot charge carriers from the channel into the gate dielectric, with temporary overloading of the field effect transistor.

When differing dielectric materials are stacked, interdiffusion may take place between the two dielectric layers due to differing lattice constants and mechanical stresses. It is also possible for impurities to be exchanged between two different dielectric layers. These and other options of influencing the dielectric are covered under the collective term of "dielectric engineering."

Mechanical stress surface conditions can be created by a difference in the lattice constants of two materials, for example, or else can be deliberately introduced by bending the substrate. Several defects can be generated by mechanical stress.

The attachment site is advantageously located no more than 2 nm away from the conducting channel of the field effect transistor so as to increase the effect of the charge exchange at the attachment site on the current by the channel. This conflicts with the customary design objectives in field effect transistors, in which the influence of random telegraph noise at defects on the current by the transistor is to be minimized.

In a particularly advantageous embodiment of the invention, the device comprises means for evaluating the time constant $\tau_c$ for the trapping and/or $\tau_e$ for the releasing of charge carriers by the attachment site from statistical step-like fluctuations of the drain current (telegraph modulation signal) that originate from the attachment site. The only unknown on which $\tau_c$ depends is the potential to be measured, or the voltage to be measured. In contrast, $\tau_e$ is not dependent on the potential or the voltage, but essentially only on the temperature. The accuracy with which the time constants can be determined increases with increasing measuring time in that the statistics improve.

For the statistical evaluation of the time constants, it is particularly advantageous when the device comprises means for evaluating the frequency distribution of variably long peaks and/or valleys in the time curve of the drain current. This not only makes different methods available for ultimately ascertaining the time constants (such as the mean value and median), but the form and extent of the distribution also supply information about the reliability and quality of the value thus ascertained. The frequency distribution is ideally a Lorentzian distribution.

The device advantageously comprises means for evaluating the frequency spectrum of the drain current. This frequency spectrum makes it possible to ascertain the cut-off frequency $f_0$ at which the telegraph modulation signal is just barely still transmitted. This cut-off frequency $f_0$ is linked by $$f_0 = \frac{\tau_c + \tau_e}{\tau_c \cdot \tau_e} = \frac{1}{\tau_c} + \frac{1}{\tau_e} \qquad (1)$$

to the two time constants $\tau_c$ and $\tau_e$. When $\tau_c \ll \tau_e$, the contribution of $\tau_e$ to $f_0$ can be neglected in equation (1), and approximately the following applies:

$$f_0 \approx \frac{1}{\tau_c} \qquad (2)$$

In most applications, $\tau_c$ is the measured variable of interest, which depends to a very high degree on the pH value of the sample, for example.

If $\tau_c$ is not very small in relation to $\tau_e$, the contribution of $\tau_0$ to $f_0$ must be considered. This contribution depends on both the temperature and the gate voltage. The measurement is therefore advantageously carried out at a temperature and/or a gate voltage in which $\tau_c \ll \tau_e$ applies, and in particular $\tau_c < 0.1 * \tau_e$.

For the approximate determination of the cut-off frequency $f_0$, it also suffices to measure the time curve, from which frequency components are subsequently extracted, instead of using a complete frequency spectrum. Since $\tau_e$ is approximately only dependent on the temperature and otherwise is constant, a measurement of $\tau_0$ at just a few different bias voltages at the gate may suffice, if the temperature is sufficiently constant, to obtain $\tau_c$ and thus the required potential or the required voltage.

The number of attachment sites that are simultaneously influenced by contact of the measuring device with the sample can be controlled by introducing, to the extent possible, only one or only a few such attachment sites into the gate dielectric. For example, the spatial dimensions of the field effect transistor can be reduced so much for this that it is very likely that at least one attachment site, but no more than just a few attachment sites, are present in the gate dielectric. Each attachment site essentially calls out the characteristic time constants thereof. If several voices can be heard, initially more such pieces of information can be transmitted simultaneously; starting at a critical number of voices, however, these can no longer be distinguished from each other, and no information at all is transmitted.

As an alternative to or in combination with making the transistor smaller or controlling the attachment sites during the production of the same, it is possible to limit the number thereof by bringing the sample in contact with the gate of the field effect transistor in an area that, in at least one Cartesian spatial dimension, measures between 20 and 500 nm, and preferably between 20 and 100 nm. In this range, it is highly likely that at least one attachment site is influenced by the sample, so that the device can supply a signal. However, it is also highly likely that no more than just a few attachment sites are influenced, so that signal contributions from differing attachment sites can still be distinguished from each other. The area in both Cartesian spatial dimensions particularly preferably measures between 20 and 500 nm, and most particularly preferably between 20 and 100 nm.

The area on which the sample comes in contact with the gate can be delimited, for example in the case of a liquid sample, by covering the gate and leaving only the defined area for access of the sample exposed. In the case of a solid sample, the area can be delimited by structuring a correspondingly small sample.

The device according to the invention can be used, for example, to detect individual molecules, such as DNA, in a liquid. Since a reliable measurement takes only a few microseconds, however, it is also possible to study dynamic phenomena in real time, such as the folding of proteins, the catalysis of reactions by enzymes, or the hybridization of DNA.

The low-noise amplifier described and claimed in the German patent application 10 2010 021 078.1 is particularly suitable for measuring the current through the transistor.

The entire disclosure provided for the device expressly also applies to the method disclosed hereafter. Conversely, the entire disclosure provided for the method expressly also applies to the device.

Within the scope of the invention, a method for measuring small voltages and potentials or other electrical variables of a sample was developed. The sample is in contact with the gate of a field effect transistor, a voltage being present between the source and the drain. Statistical step-like fluctuations (telegraph modulation signals) in the current that is driven between the source and the drain are evaluated, which originate from an attachment site that is located between the sample and the conducting channel of the field effect transistor and that traps charge carriers from the channel and, conversely, releases these to the channel.

According to the invention, the voltage or the potential is evaluated based on the time constant or constants for the trapping and/or for the releasing of charge carriers by the attachment site.

It was found that a significant portion of the information contained in the signal was discarded with the previously customary time averaging of the current driven through the transistor. The time curve of the signal contains both peaks and valleys. Both can be used to obtain information about the required potential or the required voltage. If averaging is carried out across the entire time curve, many of the peaks and valleys cancel each other out, which previously was desired. The inventors recognized, for the first time, that contrary to existing practice, the peaks and valleys are not useless. Each peak and each valley is a piece of statistics that contributes to determining the time constants $\tau_c$ and $\tau_e$, and thus improves the accuracy thereof. As a result, the required potential or the required voltage, on which $\tau_c$ depends, can also be determined with greater accuracy. At a particular measuring time, a much larger amount of information is thus utilized. Conversely, a predefined accuracy can be achieved in a shorter measuring time.

For this evaluation, advantageously at least one time constant is evaluated from the frequency distribution of variably long peaks and/or valleys in the drain current. As an alternative thereto or in combination therewith, at least one time constant is evaluated from the frequency spectrum of the drain current.

The measured potential or the measured voltage is generally not an end in itself, but a measure of a chemical or biological property of the sample, which manifests itself in a gain, a loss or spatial reorganization of charges. Since, according to the invention, the potential or the voltage can be determined more quickly and more accurately, the measurement of the ultimately required variable is also improved.

In a particularly advantageous embodiment of the invention, the pH value of the sample is evaluated from the time constant $\tau_c$ for the trapping of charge carriers by the attachment site or from the cut-off frequency $f_0$ from the frequency spectrum of the drain current. The pH value is thus directly correlated with how many hydrogen ions attach to the gate of the field effect transistor and contribute to the local potential there, it is thus directly correlated with this potential and can be evaluated, for example, from measured values for the potential. The pH value is thus an electrical variable of the sample. When the pH value is the only property of the sample of interest in the specific application, it is also possible to carry out a direct calibration based on test samples having a defined pH value, the calibration assigning exactly one pH value to each time constant $\tau_c$ or each cut-off frequency $f_0$. Based on such a calibration, the pH value can be evaluated directly from $\tau_c$ or from $f_0$, without taking an indirect approach using a voltage or a potential.

The subject matter of the invention will be described hereafter based on figures, without thereby limiting the subject matter of the invention.

BRIEF DESCRIPTION OF THE DRAWINGS

FIG. 1: shows an exemplary embodiment of the device according to the invention in a sectional drawing (sub-image a) and the time curve of the current flowing through the channel (sub-image b);

DESCRIPTION OF THE PREFERRED EMBODIMENTS

Figure 1A:
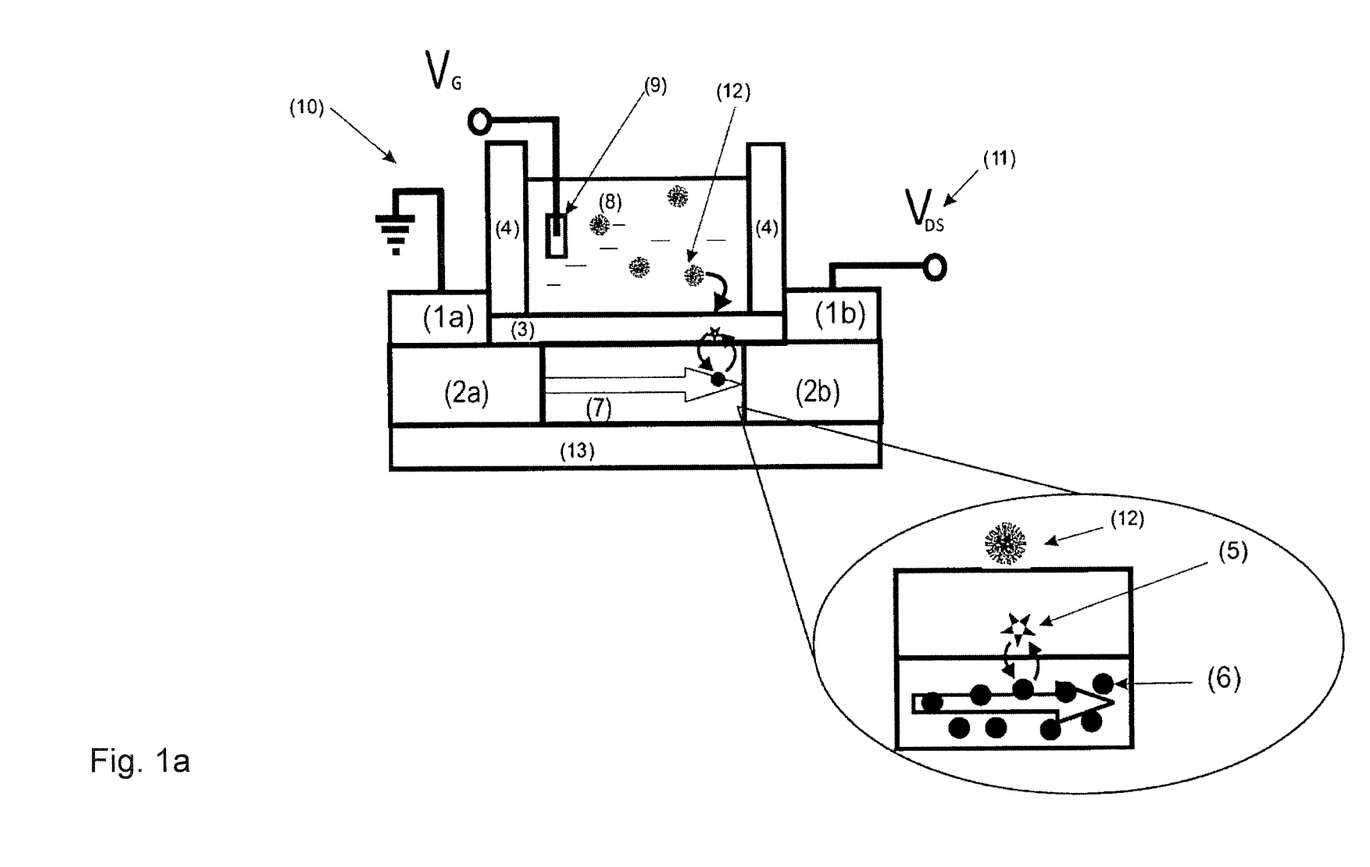

FIG. 1a shows a sectional drawing of an exemplary embodiment of the device according to the invention. Doped, highly implanted semiconducting regions 2a and 2b, which make contact with the outside via metal contacts 1a and 1b, are located on a substrate 13. A semiconducting nanochannel 7, which is doped significantly less strongly than the regions 2a and 2b, is located between the regions 2a and 2b. The contact 1a is connected to ground 10, and the contact 1b is connected to a voltage source 11 for the drain/source voltage $V_{DS}$. In this circuit, the region 2a functions as the source, the region 2b functions as the drain. The charge carriers 6 transported through the nanochannel 7 and represented there as filled-in circles are holes. The flow direction of the same is indicated by the arrow shown in the nanochannel 7.

The nanochannel 7 and parts of the regions 2a and 2b are covered by the gate dielectric 3. The gate dielectric 3 also forms the electrically insulating bottom of a reservoir 4 for the sample liquid 8. The reservoir 4 insulates the sample liquid 8 with respect to the contacts 1a and 1b. The potential of the sample liquid 8 can be set to a voltage $V_G$ via a reference electrode 9. The sample liquid 8 contains the molecules 12 to be studied.

In the interior, in the vicinity of the interface with the nanochannel 7, the gate dielectric 3 includes a point defect 5, which is able to exchange a charge carrier 6 (a hole) with the nanochannel 7. At any given point of time, the point defect 5 is either occupied by a hole 6, or it is not occupied by a hole. This is illustrated in the enlarged section.

The point defect is negatively charged when it is not occupied by a charge carrier 6 (a hole). A local depletion zone, in which holes attach and are no longer available for the current transport through the channel, forms in the channel in the vicinity of the defect.

When the point defect 5 is occupied by a charge carrier 6 (a hole), it is neutralized in terms of charge. In this case, the local depletion zone of charge carriers vanishes in the vicinity of the point defect, and the current transport through the channel is no longer impaired. A higher current thus flows through the nanochannel than when the point defect is not occupied. Statistical, step-like fluctuations between two levels are modulated onto the current flowing through the nanochannel 7 by the point defect 5 alternating between the two states "occupied" and "unoccupied" in a statistical time series.

When one of the molecules 12 to be studied attaches to the surface of the gate dielectric 3, this has two effects:

The current flowing through the nanochannel 7 is changed by a constant offset $\Delta I^b$ due to the electrostatic influence by the molecule 12.

Changes also occur in the time constants $\tau_c$ for the trapping of a hole 6 by the point defect 5 (very strong) and $\tau_e$ for the releasing of this hole 6 to the nanochannel 7 (considerably less strong). By way of the difference in the time constants, it is possible, for example, to determine the local potential at the gate changed by the sample molecule 12, the concentration of the molecules 12 in the sample liquid 8, or the pH value of the sample liquid 8.

The substrate 13 can be an undoped semiconductor, a semiconductor passivated with an oxide layer (such as an SOI substrate) or a dielectric substrate, for example.

Figure 1B:
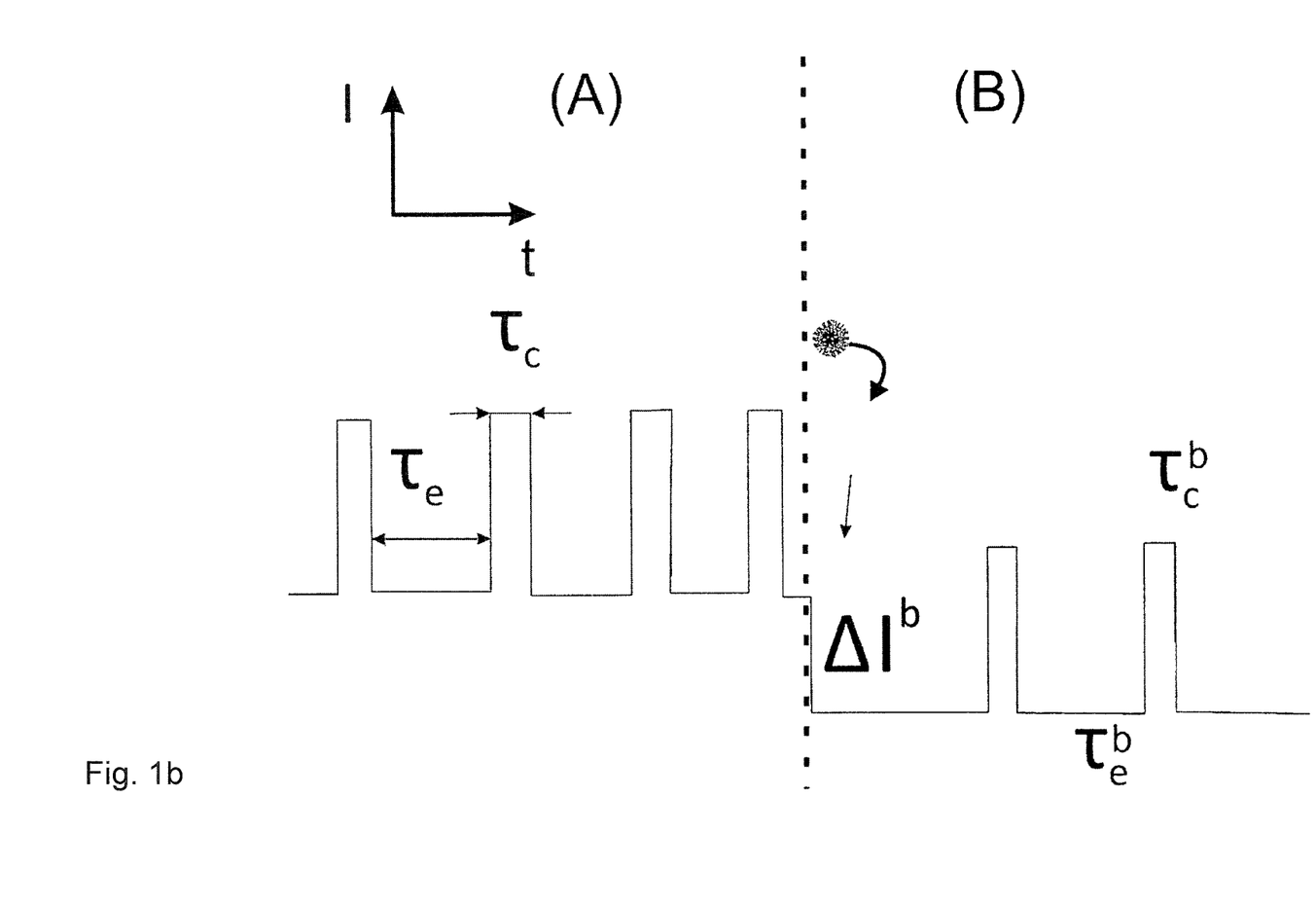

FIG. 1b shows the time curve of the current flowing through the channel without (region A) and with (region B) the sample molecule 12 attached to the surface of the gate dielectric 3. The current fluctuates statistically between two levels, which correspond to the two states "point defect 5 is occupied" and "point defect 15 is free."

The state having the higher current is present when the point defect 5 is occupied by a hole. The average duration for which this state fasts is the time constant $\tau_c$. The durations of the individual phases in which this state is present vary around the mean value $\tau_c$ with a Lorentzian distribution.

The state having the lower current is present when the point defect 5 is free. The average duration for which this state lasts is the time constant $\tau_e$. The durations of the individual phases in which this state is present vary around the mean value $\tau_e$ with a Lorentzian distribution.

Following the binding of the sample molecule 12, both the shift of the current by the offset $\Delta I^b$ and the change in the time constants $\tau_c^b$ and $\tau_e^b$ are clearly visible.

Figure 2:
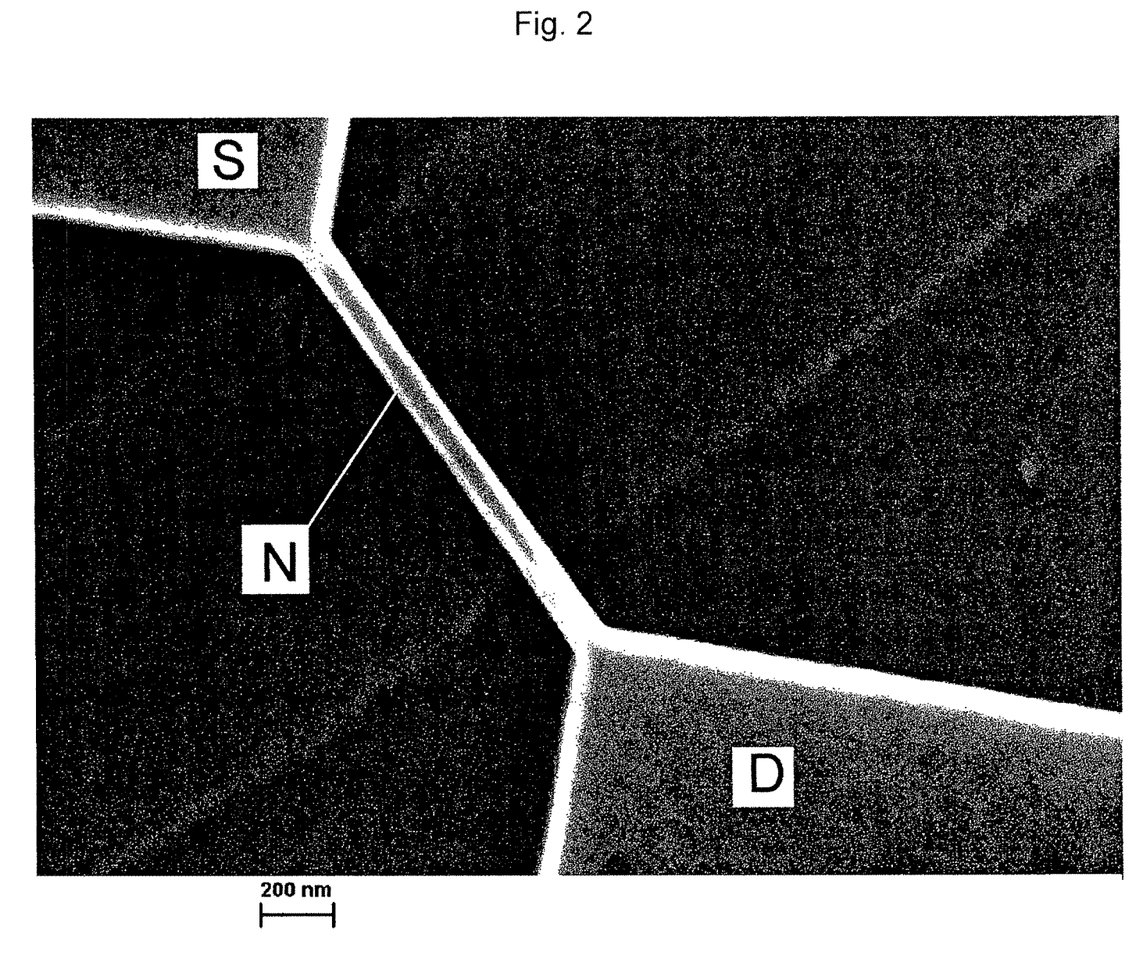
FIG. 2: shows a scanning electron microscope image of a nanowire field effect transistor as an exemplary embodiment of the device according to the invention.

FIG. 2 shows an exemplary embodiment of the device according to the invention. The figure is a scanning electron microscope image of the $p^+$-$p$-$p^+$ silicon nanowire field effect transistor. The nanowire N extending from the source S to the drain D is 500 nm long, 100 nm wide, and 50 nm thick. If is typically operated at a drain/source voltage of −0.1 V and a gate bias voltage of −0.9 V. During the measurements, the transistor was protected from the corrosive sample by a $SiO^{2-}$ passivation layer measuring 9 nm thick. The inventors anticipate the sensitivity to increase further by several orders of magnitude when the characteristic lengths of the transistors are reduced further to approximately 20 nm. In the experiments conducted by the inventors, nanoimprint methods have proven to be particularly advantageous for producing nanoscale transistors.

Figure 3:
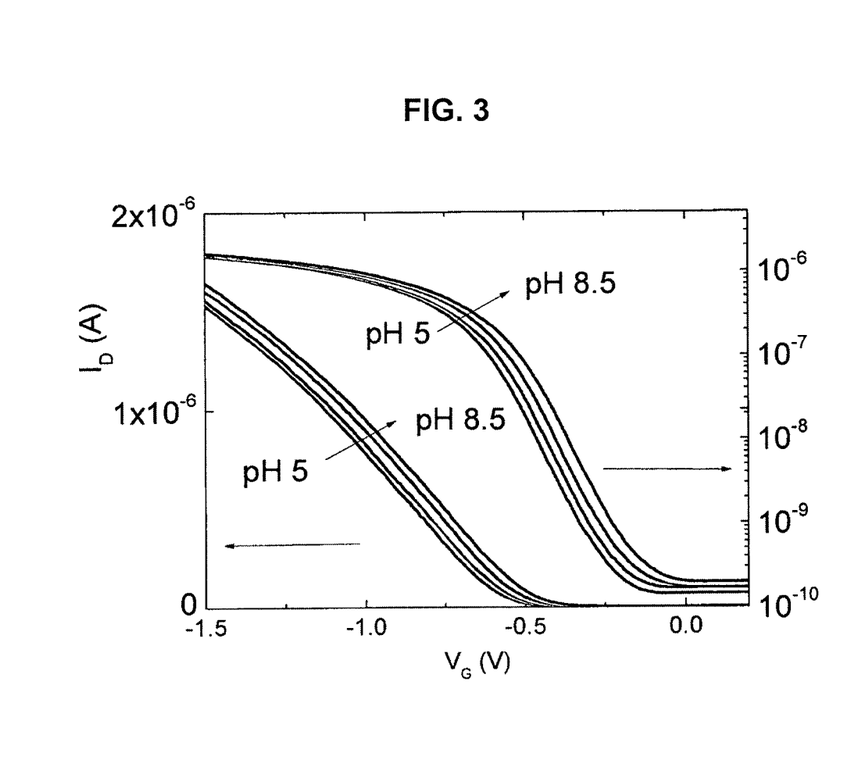
FIG. 3: shows the effect of the pH value of the sample on the functional dependence of the drain current $I_D$ on the gate voltage $V_G$.

FIG. 3 shows curves of the drain current $I_D$ as a function of the gate voltage $V_G$ preset via the reference electrode 9 for different pH values of the sample liquid 8. The current is plotted in a linear fashion for the left set of curves (left scale); the current is plotted logarithmically for the right set of curves (right scale). According to the state of the art, the pH value was evaluated based on these current profiles. Although the pH values cover a wide range between 5.5 and 8.5, the current profiles change only slightly. The measuring method according to the state of the art is therefore comparatively insensitive.

Figure 4:
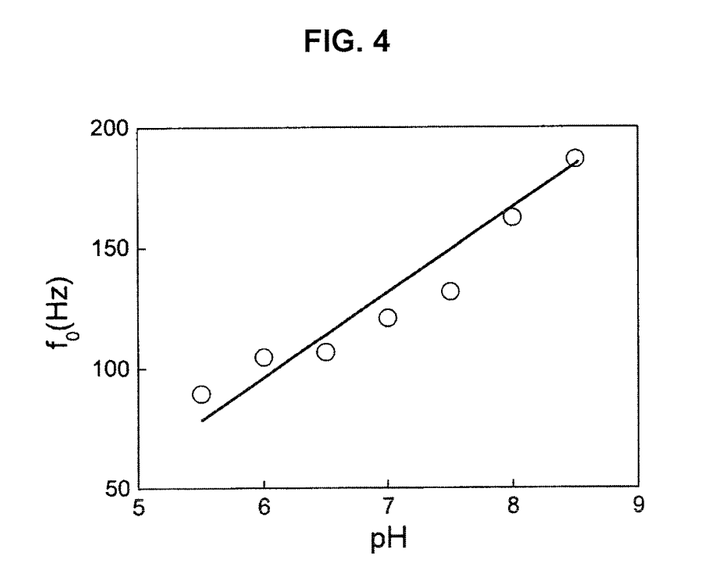
FIG. 4: shows the effect of the pH value of the sample on the cut-off frequency $f_0$ of the telegraph modulation signal.

FIG. 4 shows an exemplary embodiment of the method according to the invention, carried out using the device according to the invention. The cut-off frequency $f_0$ ascertained from the frequency spectrum of the drain current is plotted as a function of the pH value for the same pH values of the sample liquid as in FIG. 3. It was shown for the first time that a change in the pH value changes the cut-off frequency $f_0$ considerably more strongly than in the current profile shown in FIG. 3.

This change can be made even clearer by recording the frequency spectrum of the drain current several times, for example at least 10-fold, preferably at least 50-fold, and most particularly preferably at least 100-fold, and combining the individual measurements by way of averaging into a final result for the spectrum. The more individual measurements are considered in the averaging step, the more the influence of the pH value of the sample liquid on $f_0$ vanishes since $\tau_e$ is not dependent on the pH value, and the influence is purely statistical. In the example shown in FIG. 4, $\tau_e$ is in the same order of magnitude as $\tau_c$.

The extension of measuring time accompanying averaging can be counteracted by considering the spectrum only in the frequency range in which the cut-off frequency $f_0$ can vary based on a change of the pH value of the sample liquid.

Figure 5:
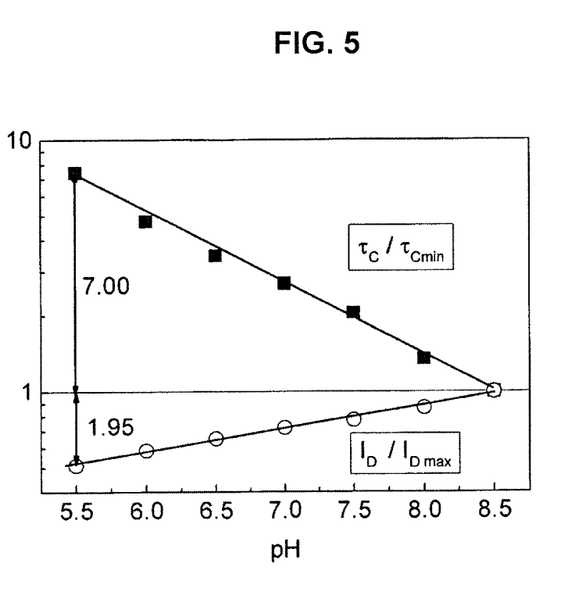
FIG. 5: shows a comparison of the sensitivity of pH measurements across the time constant $\tau_c$ of the telegraph modulation signal (top curve) and across the drain current $I_D$ (bottom curve).

In a further exemplary embodiment, FIG. 5 compares the sensitivity of the method according to the invention for measuring the pH value of a liquid sample (curve A, measuring points indicated by filled-in rectangles) to the sensitivity of a method according to the state of the art in which only the average time value of the drain current was evaluated (curve B, measuring points indicated by not filled-in circles).

Proceeding from 5.5, the pH value of the sample was increased to 8.5 in 0.5 increments. In the method according to the invention, the respective time constant $\tau_c$ for the trapping of charge carriers 6 from the channel 7 in the point defect 5 was measured. In the method according to the state of the art, the respective average time value $I_D$ of the drain current was measured, analogously to FIG. 3. The difference in the signal between the minimum and the maximum pH value is 1.95 in the method according to the state of the art; in contrast, it is 7 in the method according to the invention. The sensitivity is thus improved over the state of the art by a factor of approximately 3.5.

The pH value is thus directly correlated with how many hydrogen ions attach to the gate dielectric 3 of the field effect transistor and contribute to the changes in potential there. This affects both the drain current and the fluctuations caused by the point defect 5.

The invention claimed is:

1. A device for measuring small voltages and potentials or other electrical variables of a sample of a liquid to thereby determine properties of the sample, comprising:
   at least one field effect transistor including a source, a drain, a gate, a gate dielectric, and a conducting channel, the conducting channel being between the source and the drain; and
   a reservoir configured to receive and retain the sample; and
   a reference electrode situated in the reservoir and configured to contact the sample and to apply a reference voltage to the sample,
   wherein
   a surface of the gate dielectric comprises an interior surface of the reservoir whereby the gate dielectric is configured to be in contact with the sample received and retained in the reservoir,
   the gate dielectric and the conducting channel are configured so that the gate dielectric insulates the sample in the reservoir from the conducting channel, and an interior of the gate dielectric between the source and the drain includes at least one but no more than five local defects situated between the sample and the conducting channel which at least one but no more than five local defects are isolated from the sample and configured to provide attachment sites which are isolated from the sample and which trap charge carriers from the conducting channel and release the trapped charge carriers to the conducting channel in response to molecules in the sample approaching the gate dielectric, wherein each of the attachment sites is located in the interior of the gate dielectric and spaced from the conducting channel by no more than 2 nm, and the device further comprises means for determining at least one time constant for at least one of the trapping of the charge carriers and the releasing of the charge carriers by evaluating frequency distribution of at least one of peaks and valleys, which are variably long, in drain current of the field effect transistor or from the frequency spectrum of the drain current.

2. A method of using the device according to claim 1 for measuring small voltages and potentials or other electrical variables of a sample of a liquid thereby to determine properties of the sample, comprising introducing the sample into the reservoir, so that the sample is in contact with the gate dielectric and with the reference electrode, applying a voltage to the reference electrode so as to apply a reference voltage to the sample, evaluating statistical step-like fluctuations in a current that is driven between the drain and the source which originate from the attachment site disposed between the sample and the conducting channel of the field effect transistor, which traps charge carriers from the channel and conversely releases these to the channel, wherein the evaluating comprises determining at least one time constant for at least one of the trapping of the charge carriers and the releasing of the charge carriers by evaluating frequency distribution of at least one of peaks and valleys, which are variably long, in drain current of the field effect transistor or from the frequency spectrum of the drain current.

3. The method according to claim 2, wherein the pH value of the sample is evaluated from the time constant $\tau_c$ for the trapping of charge carriers by the attachment site or from a cut-off frequency $f_0$ from the frequency spectrum of the drain current.

4. A device for measuring small voltages and potentials or other electrical variables of a sample of a liquid to thereby determine properties of the sample, comprising:
   at least one field effect transistor including a source, a drain, a gate, a gate dielectric, and a conducting channel, the conducting channel being between the source and the drain; and
   a reservoir configured to receive and retain the sample; and
   a reference electrode situated in the reservoir and configured to contact the sample and to apply a reference voltage to the sample,
   wherein
   a surface of the gate dielectric comprises an interior surface of the reservoir whereby the gate dielectric is configured to be in contact with the sample received and retained in the reservoir,
   the gate dielectric and the conducting channel are configured so that the gate dielectric insulates the sample in the reservoir from the conducting channel, and
   an interior of the gate dielectric between the source and the drain includes local defects situated between the sample and the conducting channel which local defects are isolated from the sample and configured to provide an attachment sites which are isolated from the sample and which trap charge carriers from the conducting channel and release the trapped charge carriers to the conducting channel in response to molecules in the sample approaching the gate dielectric, wherein each of the attachment sites is located in the interior of the gate dielectric and spaced from the conducting channel by no more than 2 nm,
   and the device further comprises means for determining at least one time constant for at least one of the trapping of the charge carriers and the releasing of the charge carriers by evaluating frequency distribution of at least one of peaks and valleys, which are variably long, in drain current of the field effect transistor or from the frequency spectrum of the drain current, and
   the reservoir is configured so that the sample is in contact with the gate dielectric of the field effect transistor only in an area that, in at least one Cartesian spatial dimension, measures between 20 and 500 nm, whereby at least one but no more than five of the local defects are situated between the sample and the conducting channel.

5. The device according to claim 4, wherein the area measures between 20 and 100 nm.

6. A method of using the device according to claim 4 for measuring small voltages and potentials or other electrical variables of a sample of a liquid thereby to determine properties of molecules in the sample, comprising introducing the sample into the reservoir, so that the sample is in contact with the gate dielectric and with the reference electrode, applying a voltage to the reference electrode so as to apply a reference voltage to the sample, evaluating statistical step-like fluctuations in a current that is driven between the drain and the source which originate from the attachment site disposed between the sample and the conducting channel of the field effect transistor, which traps charge carriers from the channel and conversely releases these to the channel, wherein the evaluating comprises determining at least one time constant for at least one of the trapping of the charge carriers and the releasing of the charge carriers by evaluating frequency distribution of at least one of peaks and valleys, which are variably long, in drain current of the field effect transistor or from the frequency spectrum of the drain current.

7. The method of using the device according to claim 6, wherein the pH value of the sample is evaluated from the time constant $\tau_c$ for the trapping of charge carriers by the attachment site or from a cut-off frequency $f_0$ from the frequency spectrum of the drain current.

8. A device for measuring small voltages and potentials or other electrical variables of a sample of a liquid to thereby determine properties of the sample, comprising:
  at least one field effect transistor including a source, a drain, a gate, a gate dielectric, and a conducting channel, the conducting channel being between the source and the drain; and
  a reservoir configured to receive and retain the sample; and
  a reference electrode situated in the reservoir and configured to contact the sample and to apply a reference voltage to the sample,
  wherein
  a surface of the gate dielectric comprises an interior surface of the reservoir whereby the gate dielectric is configured to be in contact with the sample received and retained in the reservoir,
  the gate dielectric and the conducting channel are configured so that the gate dielectric insulates the sample in the reservoir from the conducting channel, and
  an interior of the gate dielectric between the source and the drain includes local defects situated between the sample and the conducting channel which local defects are isolated from the sample and configured to provide an attachment sites which are isolated from the sample and which trap charge carriers from the conducting channel and release the trapped charge carriers to the conducting channel in response to molecules in the sample approaching the gate dielectric, wherein each of the attachment sites is located in the interior of the gate dielectric and spaced from the conducting channel by no more than 2 nm,
  and the device further comprises means for determining at least one time constant for at least one of the trapping of the charge carriers and the releasing of the charge carriers by evaluating frequency distribution of at least one of peaks and valleys, which are variably long, in drain current of the field effect transistor or from the frequency spectrum of the drain current, and
  the field effect transistor is so small that at least one but no more than five of the local defects are situated between the sample and the conducting channel.

9. The method of using the device according to claim 8 for measuring small voltages and potentials or other electrical variables of a sample of a liquid thereby to determine properties of molecules in the sample, comprising introducing the sample into the reservoir, so that the sample is in contact with the gate dielectric and with the reference electrode, applying a voltage to the reference electrode so as to apply a reference voltage to the sample, evaluating statistical step-like fluctuations in a current that is driven between the drain and the source which originate from the attachment site disposed between the sample and the conducting channel of the field effect transistor, which traps charge carriers from the channel and conversely releases these to the channel, wherein the evaluating comprises determining at least one time constant for at least one of the trapping of the charge carriers and the releasing of the charge carriers by evaluating frequency distribution of at least one of peaks and valleys, which are variably long, in drain current of the field effect transistor or from the frequency spectrum of the drain current.

10. The method of using the device according to claim 9, wherein the pH value of the sample is evaluated from the time constant $\tau_c$ for the trapping of charge carriers by the attachment site or from a cut-off frequency $f_0$ from the frequency spectrum of the drain current.

* * * * *